United States Patent [19]
Sakurai et al.

[11] Patent Number: 5,310,881
[45] Date of Patent: May 10, 1994

[54] GLYCOSAMINOGLYCAN-MODIFIED PROTEIN

[75] Inventors: Katsukiyo Sakurai; Kyosuke Miyazaki, both of Tokyo, Japan

[73] Assignee: Seikagaku Corporation, Tokyo, Japan

[21] Appl. No.: 908,910

[22] Filed: Jul. 2, 1992

Related U.S. Application Data

[63] Continuation of Ser. No. 596,830, Oct. 12, 1990, abandoned.

[30] Foreign Application Priority Data

Mar. 30, 1990 [JP] Japan .................. 2-081163

[51] Int. Cl.$^5$ ............................................. C07K 15/14
[52] U.S. Cl. ............................................. 530/395
[58] Field of Search ............................................. 530/395

[56] References Cited

U.S. PATENT DOCUMENTS

| | | | |
|---|---|---|---|
| 2,824,092 | 2/1958 | Thompson | 530/395 |
| 4,055,635 | 10/1977 | Green et al. | 424/78 |
| 4,301,153 | 11/1981 | Rosenberg | 536/21 X |
| 4,356,170 | 10/1982 | Jennings et al. | 424/92 |
| 4,496,550 | 1/1985 | Lindahl et al. | 536/21 X |
| 4,526,714 | 7/1985 | Feijen et al. | 530/395 |
| 4,585,754 | 4/1986 | Meisner et al. | 514/8 |
| 4,613,665 | 9/1986 | Larm | 536/21 X |
| 4,745,180 | 5/1988 | Moreland et al. | 530/395 X |
| 4,863,907 | 9/1989 | Sakurai et al. | 536/21 X |
| 4,920,194 | 4/1990 | Feller et al. | 514/6 |

FOREIGN PATENT DOCUMENTS

| | | |
|---|---|---|
| 0081853 | 6/1983 | European Pat. Off. . |
| 0344068 | 11/1989 | European Pat. Off. . |
| 0345616 | 12/1989 | European Pat. Off. . |
| 8909624 | 10/1989 | PCT Int'l Appl. . |
| 9001332 | 2/1990 | PCT Int'l Appl. . |

OTHER PUBLICATIONS

Chemical Abstracts, vol. 103, No. 21, Nov. 25, 1985, p. 45, Abstract No. 171707k, Columbus, Ohio, US; A. V. Maksimenko et al.: "Water-soluble urokinase conjugates: fibrinolytic activity and other properties", & Vopr. Med. Khim. 1985, 31(4), 12–20.
M. Okada et al., In. Archs. Allergy appl. Immun., 76, 79–81 (1985).
F. T. Liu et al., Proc. Natl. Acad. Sci. USA, 76 (3), 1430–1434 (1979).
H. Maeda et al., J. Med. Chem., 28, 455–461 (1985).
T. P. King et al., Arch. Biochem. Biophys., 169, 464–473 (1975).
M. Usui et al., J. Immunol., 122 (4), 1266–1272 (1979).
Genkansa Ryoho no Kiso to Rinsho, ed. by S. Kobayashi et al., Chugai Igakusho (1982), pp. 4–11 (together with an English translation of the relevant portion).

*Primary Examiner*—Michael G. Wityshyn
*Assistant Examiner*—C. Sayala
*Attorney, Agent, or Firm*—Sughrue, Mion, Zinn, Macpeak & Seas

[57] ABSTRACT

A glycosaminoglycan-modified protein wherein an amino group of a protein is bound to an aldehyde group, which has been formed by reducing and partially oxidizing the reducing terminal sugar moiety of a glycosaminoglycan, which has a high stability in vivo and can retain physiological activity of the protein for a prolonged period of time.

7 Claims, 4 Drawing Sheets

FIG.4A
ALUCIAN BLUE STAINING

FIG.4B
PONCEAU 3R STAINING

FIG.5A
TOLUIDINE BLUE STAINING

FIG.5B
COOMASSIE BLUE STAINING

FIG.6A

COOMASSIE BLUE STAINING

FIG.6B

ALUCIAN BLUE & TOLUIDINE BLUE STAINING

GLYCOSAMINOGLYCAN-MODIFIED PROTEIN

This is a continuation of application Ser. No. 07/596,830 filed Oct. 12, 1990, now abandoned.

FIELD OF THE INVENTION

This invention relates to a protein modified with a glycosaminoglycan. More particularly, it relates to a protein modified with a glycosaminoglycan which is obtained by reacting a glycosaminoglycan activated with a specific activator with a protein.

BACKGROUND OF THE INVENTION

Recently, attempts have been frequently made to apply enzymes and physiologically active proteins as drugs for treating various diseases including cancer, inflammation and hereditary enzyme deficiency.

However, many of these enzymes and physiologically active proteins are heterogenic to living organisms. Thus the administration of these compounds as such to an organism would cause a problem of immunogenicity or deteriorate the stability in vivo. When such a compound is to be formulated into a medicine, therefore, it is required to relieve an anaphylatic reaction and to improve the prolonged drug effect.

Furthermore, attempts have been made to produce these proteins in a large amount through genetic engineering techniques. However, proteins produced by genetic engineering suffer from a problem of the deficiency of a sugar chain, which seriously affects the stability in vivo.

Accordingly, there has been proposed to modify an enzyme or a physiologically active protein with various synthetic polymers or polysaccharides so as to pharmacologically improve the stability thereof. Examples of the synthetic polymers employed therefor include poly-L-aspartic acid (M. Okada, A. Matsushima, A. Katsuhata, T. Aoyama, T. Ando and Y. Inada: Int. Archs Allerlrgy Appl. Immun. 76, 79–81 (1985)) and derivatives thereof, poly-D- or -L-lysine, D-glutamic acid/D-lysine copolymer (F. T. Liu and D. H. Katz: Proc. Natl. Acad. Sci. USA, 76, 1430–1434 (1979)), polyvinyl alcohol pyran copolymer, polyethylene glycol and derivatives thereof and styrene/maleic acid copolymer (H. Maeda, M. Ueda, T. Morinaga and T. Matsumoto: J. Med. Chem., 28, 455–461 (1985)). Examples of the polysaccharides include agarose, carboxymethyl cellulose, dextran (T. P. King, L. Kochoumian, K. Ishizaka, L. Kichtenstein, P. S. Norman: Arch. Biochem. Biophys., 169, 464–473 (1975)), pullulan (M. Usui and T. Matsuhashi: J. Immunol., 122, 1266–1272 (1979) and N. Matsuhashi: Genkansa no Jikken Dobutsu Moderu (Experimental Animal Model for Hyposensitization), ed. by S. Kobayashi et al., Genkansa Ryoho no Kiso to Rinsho (Bases and Clinical Application of Hyposensitization Therapy), 4–11, Chugai Igakusho (1982)) and lipopolysaccharide.

On the other hand, U.S. Pat. No. 4,585,754 proposes a stabilized protein which is obtained by reacting a protein such as superoxide dismutase or insulin with chondroitin sulfate in the presence of 1-ethyl-3-(3-dimethylaminopropyl)carbodiimide. However, the protein thus obtained is in the form of a complicated polymer involving a polymer of the protein per se, since plural carboxyl groups in aspartic acid or glutamic acid contained in the protein are activated by 1-ethyl-3-(3-dimethylaminopropyl)carbodiimide, respectively. Thus, this product should be further improved from the viewpoint of the pharmacological effect of the unmodified superoxide dismutase or insulin as a monomer.

SUMMARY OF THE INVENTION

An object of the present invention is to provide a glycosaminoglycan-modified protein, which is highly stable in vivo and can express the inherent physiological effect of the starting protein for a prolonged period of time without forming any polymer of a complicated structure.

The above object of the present invention can be achieved by a glycosaminoglycan-modified protein obtained by reacting glycosaminoglycan activated by reducing terminal residue-limiting oxidation method, carboxyl group-activating method, reducing terminal residue-lactonization method or cyanogen bromide activation method with a protein.

According to an embodiment of the present invention, a glycosaminoglycan-modified protein wherein an amino group of a protein is bound to an aldehyde group, which has been formed by reducing and partially oxidizing the reducing terminal sugar moiety of a glycosaminoglycan is provided.

According to another embodiment of the present invention, a glycosaminoglycan-modified protein of the following formula:

wherein P represents a protein residue exclusive of n amino groups from the protein; and GAG represents a glycosaminoglycan residue exclusive of the reducing terminal sugar moiety from the glycosaminoglycan.

According to another embodiment of the present invention, a glycosaminoglycan-modified protein wherein at least some of carboxyl groups in the uronic acid moiety of a glycosaminoglycan are bound to a protein via an amide bond.

BRIEF DESCRIPTION OF THE DRAWINGS

In FIGS. 1A and B, Lane 1 stands for the electrophoretic pattern of a mixture of bovine-derived catalase and hyaluronic acid (HA) the reducing terminal residue of which was limitedly oxidized (O-HA) and Lane 2 stands for the pattern of HA-modified bovine-derived catalase.

In FIGS. 2A and B, Lane 1 stands for the electrophoretic pattern of a mixture of *Aspergillus niger*-derived catalase and O-HA and Lane 2 stands for the pattern of HA-modified *Asoerugillus niger*-derived catalase.

In FIGS. 3A and B, Lane 1 stands for the electrophoretic pattern of a mixture of uricase and O-HA and Lane 2 stands for the pattern of HA-modified uricase.

In FIGS. 4A and B Lane 1 stands for the electrophoretic pattern of a mixture of asparaginase and O-HA and Lane 2 stands for the pattern of HA-modified asparaginase.

In FIGS. 5A and B, Lane 1 stands for the electrophoretic pattern of a mixture of superoxide disumutase (SOD) and chondroitin sulfate derived from bovine tracheal cartilages the reducing terminal residue of which was limitedly oxidized (O-CS(T)) and Lane 2 stands for the pattern of CS(T)-modified SOD (Lot No. 121-2).

In FIGS. 6A and B, Lane 1 stands for the electrophoretic pattern of SOD derived from bovine red blood cell, Lane 2 stands for the pattern of SOD derived from dog red blood cell, Lane 3 stands for the pattern of HA-modified SOD derived from dog red blood cell, and Lane 4 stands for HA-modified SOD derived from bovine red blood cell.

In FIG. 7, Lane S stands for CS(T), Lanes 1, 2, 3, 4, 5, 6 and 7 each stands for CS(T) treated with 0.0436 mg, 0.145 mg, 0.436 mg, 1.45 mg, 4.36 mg, 14.5 mg and 43.6 mg of water-soluble carbodiimide (WSC), respectively, and Lane 8 stands for CS(T) treated with 43.6 mg of WSC and 0.1N sodium hydroxide.

In FIG. 8, A is a chromatogram for a mixture of chondroitin sulfate originating from bovine tracheal cartilages and superoxide dismutase, B for the product of the lot No. B, C for the product of the lot No. C and D for the product of the lot No. 121-2 prepared in Example 2.

Unless otherwise stated, reference to the individual figures; e.g., FIG. 1, should be understood to encompass both sections of the figure, e.g., FIGS. 1A and 1B.

DETAILED DESCRIPTION OF THE INVENTION

The glycosaminoglycan-modified protein of the present invention may be produced by, for example, reacting a glycosaminoglycan activated by reducing terminal residue-limiting limiting oxidation method, reducing terminal residue-lactonization method, carboxyl group activating method or cyanogen bromide activation method with a protein.

The process for production of glycosaminoglycan-modified protein of the present invention is described in detail below.

Reducing terminal residue-limiting oxidation method

This method comprises reducing and partially oxidizing the reducing terminal sugar moiety of a glycosaminoglycan to thereby cleave said terminal sugar moiety and form an aldehyde group and producing a protein modified with the glycosaminoglycan by the reducing alkylation reaction between the aldehyde group and an amino group of the protein. The reaction scheme of this method is as follows:

Reaction scheme A

In the above reaction scheme, $R^1$ and $R^2$ each represents groups commonly observed at the 2- and 5-positions of the reducing terminal sugar moiety of a glycosaminoglycan and examples of $R^1$ include OH, $NH_2$ and $NHCOCH_3$ while examples of $R^2$ include $CH_2OH$, COOH and $CH_2OSO_3M$, wherein M represents a hydrogen atom, an alkali or alkaline earth metal or an amine such as trialkylamine or pyridine; and P, n and GAG are as defined above.

In this method, the glycosaminoglycan of the above formula (IV) is first reduced to thereby cleave the reducing terminal sugar moiety thereof. Thus the compound of the formula (V) is obtained. Examples of the reducing agent to be used in this reduction step include alkali boron hydrides such as sodium boron hydride and sodium boron cyanohydride. The above reduction may be effected in an appropriate liquid medium, for example, a buffer solution such as borate buffer solution (pH 8.3), phosphate buffer solution (pH 8.6) or a mixture of such a buffer solution with an organic solvent such as dimethylformamide, acetonitrile or dioxane methanol usually at a temperature of from 0° to 40° C., preferably from 15° to 20° C.

The amount of the above-mentioned reducing agent may vary depending on the type. It may be used in an amount of from 5 to 50 equivalents, preferably from 10 to 20 equivalents, per mole of the compound of the formula (IV).

Next, the compound of the formula (V) thus obtained is partially oxidized. When $R^1$ in the formula (V) is an OH group, an aldehyde compound of the formula (VI)

is formed by this oxidation. When the R² in the formula (V) is a CH₂OH group, on the other hand, an aldehyde compound of the formula (VII) is formed. Examples of the oxidizing agent to be used in this oxidation include alkali periodates such as sodium periodate or potassium periodate. The oxidizing agent may be employed usually in an amount of from 1 to 30 equivalents, preferably from 5 to 10 equivalents, per one mole of the compound of the formula (V). The above-mentioned oxidation may be conducted generally at a temperature of from 0° to 20° C., preferably from 0° to 5° C.

The aldehyde compound of the formula (VI) or (VII) thus obtained may be reacted with an amino group of a protein by a known reducing alkylation method. Thus, the desired glycosaminoglycan-modified protein of the present invention represented by the formula (I) or (II) may be obtained. The reducing alkylation may be conducted by reacting the aldehyde compound of the formula (VI) or (VII) with the protein in a liquid medium selected from, for example, the above-mentioned ones usually at a temperature of from 15° to 60° C. Simultaneously with this reaction or after the completion the reaction, the reaction mixture is subjected to reduction with a reducing agent such as sodium boron cyanohydride.

Regarding the glycosaminoglycan-modified protein of the formula (I) or (II), n may generally range from an integer of 1 to 100, preferably from 1 to 10 on average.

Reducing terminal residue-lactonization method

This method comprises partially oxidizing the reducing terminal sugar moiety of a glycosaminoglycan to thereby cleave the terminal sugar moiety followed by forming a lactone. Then, a protein modified with the glycosaminoglycan is prepared by reacting the lactone with an amino group of the protein. The reaction scheme of this method is as follows:

Reaction Scheme B

-continued
Reaction Scheme B

In the above reaction scheme, A represents a potassium or sodium atom; and P. n, GAG, R¹ and R² are as defined above.

In this method, the glycosaminoglycan of the formula (IV) is first oxidized to cleave the reducing terminal sugar moiety. Thus, a carboxyl compound of the formula (VIII) is obtained. Example of the oxidizing agent to be used in this oxidation step include iodine and bromine. The oxidizing agent may be used usually in an amount of from 2 to 20 equivalents, preferably from 5 to 15 equivalents, per mole of the compound of the formula (IV). The oxidation reaction may be conducted in a liquid medium selected from among, for example, the above-mentioned ones at a temperature of from 0° to 40° C., preferably from 15° to 20° C. After the oxidation reaction, potassium hydroxide or sodium hydroxide is added to the reaction mixture to decompose the remaining oxidizing agent.

The thus-obtained solution containing the compound of the formula (VIII) is applied to a column packed with 200 ml of strongly acidic cation exchange resins such as Dowex 50 and Amberlite IR120 and allowed it to pass through the column over 1 hour to obtain the passed-through fraction. The column is washed with water, this water fraction is combined with the above-obtained passed-through fraction and then the combined fraction is allowed to stand overnight at 4° C. to form the lactone compound of the formula (IX).

The lactone compound of the formula (IX) thus obtained is then reacted with a protein to give the glycosaminoglycan-modified protein represented by the formula (III). The reaction between the lactone compound of the formula (IX) and the protein may be conducted by reacting the lactone in the form of a trialkylamine or adjusting the pH value of a mixture of the lactone and the protein to 4 to 7 with an aqueous solution of sodium hydroxide followed by effecting the reaction at 0° to 70° C., preferably 15° to 50° C.

Regarding the glycosaminoglycan-modified protein of the formula (III), n may generally range from an integer of 1 to 100, preferably from 1 to 10 on average.

Carboxyl group-activating method

With a few exceptions (e.g., keratosulfate and keratopolysulfate), glycosaminoglycans carry each an uronic acid moiety represented by the following formula:

According to this method, the protein modified with the glycosaminoglycan can be obtained by binding a carboxyl group in the uronic acid moiety of a glycosaminoglycan to an amino group of the protein.

This method comprises activating a carboxyl group in an uronic acid moiety of a glycosaminoglycan by a method widely known in peptide chemistry and then reacting the carboxyl group thus activated with a protein.

The carboxyl group in the uronic acid moiety of the glycosaminoglycan may be activated by, for example, reacting the glycosaminoglycan with a compound selected from N-hydroxysuccinimide, p-nitrophenol, N-hydroxybenzotriazole, N-hydroxypiperidine, and 2,4,5-trichlorophenol to convert the carboxyl group into an active ester group.

More particularly, the glycosaminoglycan is converted into a salt with an appropriate amine such as tri(n-butyl)amine, triethylamine, pyridine. Then, the resulting salt is reacted with N-hydroxysuccinimide in an appropriate solvent such as dimethylformamide, pyridine, dimethylsulfoxide in the presence of a condensation agent such as 1-ethyl-3-(dimethylaminopropyl)-carbodiimide, dicyclohexylcarbodiimide at a temperature of from 0° to 50° C. Thus, a glycosaminoglycan having an activated carboxyl group is obtained.

Then, the glycosaminoglycan having an activated carboxyl group is reacted with a protein to give the glycosaminoglycan-modified protein of the present invention.

Namely, an aqueous solution of the protein is added to an aqueous solution of the glycosaminoglycan having an activated carboxyl group or a phosphate buffer solution (pH 6 to 9) containing the glycosaminoglycan having an activated carboxyl group and the mixture is allowed to react at 0° to 50° C., preferably 15° to 25° C., for 30 minutes to 20 hours.

The above-mentioned carboxyl group-activating method makes it possible to obtain a glycosaminoglycan-modified protein wherein at least some of carboxyl groups in the uronic acid moiety of the glycosaminoglycan are bound to the protein via an amide bond.

Cyanogen bromide activation method

This method comprises activating an amino group or a carboxyl group of a protein, or a carboxyl group, a hydroxyl group or an functional group in the reducing terminal residue of a glycosaminoglycan and then allowing the mixture to react to bind the glycosaminoglycan to the protein.

More specifically, the glycosaminoglycan-modified protein can be obtained according to this method as follows.

Glycosaminoglycan is dissolved in 2M phosphate buffer (pH 11.5) and an acetonitrile solution of cyanogen bromide is added thereto. After reacting the mixture at 4° C. for 5 minutes, acetonitrile is added to the reaction mixture to give a precipitate. After removal of excessive cyanogen bromide, the precipitate is dissolved in 0.1M sodium hyrogencarbonate solution. A protein was added thereto and a reaction is carried out at 4° C. for 20 hours to obtain a desired product.

The glycosaminoglycan-modified protein produced by one of the above-mentioned methods may be separated and purified by a conventional method. For example, the reaction mixture is desalted with the use of a dialysis membrane or an ultrafiltration membrane. Then, the desired product is separated from the unreacted glycosaminoglycan and protein and purified with the use of an anion exchanger or a cation exchanger. Alternately, the product may be separated and purified by gel filtration by taking advantage of the difference in molecular weight. In the cases of some proteins, furthermore, it is possible to separate and purify the desired product by affinity chromatography using a carrier on which an enzyme inhibitor, a substrate or an antibody is immobilized.

The glycosaminoglycan employed in the present invention for modifying a protein may be selected over a wide range depending on the required characteristics of the desired glycosaminoglycan-modified protein and the purpose of the modification, without particular restriction. More particularly, it may be selected from among colominic acid, hyaluronic acid, chondroitin, chondroitin sulfate, teichuronic acid, dermatan sulfate, heparin, heparan sulfate, keratosulfate, keratopolysulfate and derivatives thereof such as chondroitin polysulfate. When the desired product is used as an antithrombotic agent and an antiarteriosclerotic agent, preferred glycosaminoglycans are chondroitin sulfate, chondroitin polysulfate, heparin, heparan sulfate and dermatan sulfate. On the other hand, hyaluronic acid, dermatan sulfate and chondroitin sulfate are suitable for the production of an antirheumatic agent and an antiinflammatory agent. These glycosaminoglycans can be used alone or in combination of two or more.

The protein to be modified with the glycosaminoglycan is not particularly restricted. Usable as the proteins are physiologically active proteins originating from various animals including human, microorganisms and plants as well as those produced by chemical synthesis or using genetic engineering techniques. Specific examples of the proteins include cytokines (for example, various interferons such as interferon-$\alpha$, interferon-$\beta$ and interferon-$\gamma$, interleukin-2, interleukin-3), hormones [for example, insulin, growth hormone-releasing factor (GRF), calcitonin, calcitonin gene-relating peptide (CGRP), atrial natriuretic hormone (ANP), vasopressin, corticotropin-releasing factor (CRF), vasoactive intestinal peptide (VIP), secretin, $\alpha$-melanocyte-stimulating hormone ($\alpha$-MSH), adrenocorticotropic hormone (ACTH), cholecystokinin (CCK), glucagon, parathyroid hormone (PTH), parathyroid hormone-relating protein (PTHrP), somatostatin, enkephalin], growth factors [for example, growth hormone (GH), insulin-like growth factor (IGF-I, IGF-II), $\beta$-nerve growth factor ($\beta$-NGF), basic fibroblast growth factor (bFGF), transforming growth factor-$\beta$ (TGF-$\beta$), erythropoietin, granulocyte colony stimulating factor (G-CSF), granulocyte macrophage colony stimulating factor (GM-CSF), platelet-derived growth factor (PDGF), epidermal growth factor (EGF)], enzymes [for example, tissue plasminogen activator (TPA), elastase, superoxide dismutase (SOD), bilirubin oxidase, catalase, uricase, urokinase, thermolysin, trypsin, chymotrypsin, Vs protease, pepsin, papain, hyaluronidase, chondroitin ABC lyase, asparaginase] and other proteins [for example, ubiquitin, insulin secretion-activating protein (IAP), serum thymus factor (STF), peptide-T, albumin, globulin, transferrin, lipoprotein, lipid A derivative, Ornithonyssus protein, trypsin inhibitor].

In the glycosaminoglycan-modified protein of the present invention, a glycosaminoglycan residue is chemically bound to a protein. The amount of the glycosaminoglycan to be introduced into the protein may vary depending on, for example, the protein and/or glycosaminoglycan, its molecular weight and the final usage of the formed glycosaminoglycan-modified protein. However, the suitable introduction amount of each gycosaminoglycan may be easily determined by those skilled in the art by simple experiments. Generally, the glycosaminoglycan may be introduced into the protein in an amount of from 1 to 99.9% by weight, preferably from 90 to 95% by weight, based on the weight of the protein to be modified.

A glycosaminoglycan-modified protein hardly react with the antibody corresponding to the unmodified protein. Furthermore, the antibody productivity of the protein is substantially lowered by the modification as described in the following Examples.

Further, when the glycosaminoglycan-modified protein is administered to a living organism, its activity is sustained for a long time, compared with the activity of the corresponding unmodified protein. Thus, the glycosaminoglycan-modified protein shows an improved stability in vivo.

Drugs containing the glycosaminoglycan-modified protein of the present invention may be formulated into various forms for oral administration, for example, granules, fine subtilaes, powders, tablets, capsules, syrups, troches, suspensions or solutions. Alternately, the glycosaminoglycan-modified protein may be orally administered as such. Alternately, it may be formulated into injections for intravenous, intra-arterial, intraportal, intrapleuroperitoneal, intramuscular, subcutaneous or intratumor administration. Furthermore, it may be in the form of a powder and formulated into an injection upon use. It may be formulated into suppositories for per rectum or ointments for parenteral administration. These preparations may be formulated together with known organic or inorganic liquid or solid pharmaceutical carriers, diluents, binders, disintegrating agents and the like suitable for oral, parenteral or per rectum administration. (e.g., lactose, sucrose, glucose, starch, gum arabic, tragacanth gum). Furthermore, stabilizers, humectants, emulsifiers, aromatics and components for varying osmotic pressure may be added thereto. Examples thereof include gelatin, glycerol, vaseline, wax, plastics and higher alcohol. Furthermore, salts may be optionally used as an assistant ingredient for maintaining the pH value of the formulation at an appropriate level. For suppositories, a water-soluble or hydrophilic base such as macrogol or an oily base such as cacao oil may be used.

The dose of the glycosaminoglycan-modified protein of the present invention may vary depending on the disease to be treated and symptoms and age of the patient. It is preferable to continuously or intermittently administer the compound to a patient in a dose of from 1 to 5000 mg/day in the case of oral administration or from 1 to 100 mg/day in the case of injection.

To further ilustrate the present invention, and not by way of limitation, the following Examples are given.

In the following Examples, the activity and molecular weight of the GAG-modified proteins and the content of glycosaminoglycans and proteins were determined under the following conditions.

DETERMINATION OF ACTIVITY

| |
|---|
| Catalase: |
| One unit (U) of enzyme is defined as the amount of the enzyme decomposing 1.0 μM of hydrogen peroxide in a hydrogen peroxide solution having a hydrogen peroxide concentration ranging from 9.2 to 10.3 mM per minute at pH 7.0 and 25° C. |
| Lysozyme: |
| One unit of enzyme is defined as the amount of the enzyme that produced a decrease in absorbance of 0.001 of a suspension of a gram-positive bacterium (ML-Cell) at 540 nm per minute at pH 6.2 and 35° C. |
| Hyaluronidase: |
| One unit of enzyme is defined as the amount of the enzyme liberating 1 μM of an unsaturated disaccharide from hyaluronic acid per minute at pH 6.2 and 37° C. |
| Elastase: |
| One unit of enzyme is defined as the amount of the enzyme hydrolyzing 1 μM of N-acetyl-tri-L-alanine methyl ester per minute at pH 8.5 and 25° C. |
| Uricase: |
| One unit of enzyme is defined as the amount of the enzyme oxidizing 1 μM of uric acid per minute at pH 8.5 and 25° C. |
| Urokinase: |
| One unit of enzyme is defined as the amount of the enzyme that produced a plasminogen, when plasminogen is treated with urokinase at pH 7.5 and 37° C., which gives a change of 1.0 of an absorbance of a substance soluble in perchloric acid formed from α-casein per minute at $\Delta_{275}$. |
| Asparaginase: |
| One unit of enzyme is defined as the amount of the enzyme producing 1.0 μM of ammonia from L-aspargine per minute at pH 8.6 and 37° C. |
| Superoxide dismutase: |
| One unit of enzyme is defined as the amount of the enzyme inhibiting 50% of the activity of xanthine oxidase at pH 7.8 and 25° C. |

DETERMINATION OF MOLECULAR WEIGHT

A sample is subjected to high performance liquid chromatography using a G6000PWx2 (Tosoh Corporation) column. Elution was carried out with a 0.2M sodium chloride aqueous solution. The molecular weight of a sample is determined based on a calibration curve.

DETERMINATION OF CONTENT OF GLYCOSAMINOGLYCAN (1) Glycosaminoglycan containing uronic acid A sample is subjected to carbazole-sulfuric acid reaction in accordance with the method as described in T. Bitter and H. M. Muir, Analytical Biochemistry, 4, 330–334 (1962).

(2) Glycosaminoglycan containing no uronic acid

A sample is subjected to phenol-sulfuric acid reaction in accordance with the method described in M. Dubois, K. A. Gilles, J. K. Hamilton, P. A. Rebers and F. Smith, Anal. Chem., 28, 350–356 (1956).

Determination of content of protein

The content of a protein is determined by the method of Lowry et al. as described in O. H. Lowry, N. J. Rosenbrough, A. L. Farr and R. J. Randall, J. Biol. Chem., 193, 265–275 (1951).

EXAMPLE 1

Preparation of GAG-modified protein by reducing terminal residue-limiting oxidation method A. Preparation of reducing terminal residue-limiting oxidized glycosaminoglycan I. Preparation of reducing terminal residue-cleaved hyaluronic acid (R-HA)

2000 mg of hyaluronic acid (MW 10000) was dissolved in 200 ml of a 0.05M borate buffer solution (pH 8.3) and 182 mg of sodium borohydride was added thereto. The mixture was allowed to react at room temperature for 5 hours. The pH value of the reaction mixture was adjusted to 4.5 with acetic acid and ethanol was added. The precipitate thus formed was collected by filtration and dissolved in 200 ml of water. Then, the resulting solution was passed through a column packed with 1000 ml of a cation exchange resin [Dowex 50 ($H^+$)]. The eluate and water used to wash the column were combined and ethanol saturated with sodium acetate was added. The precipitate thus formed was collected by filtration.

Lot No. 100.
Yield: 1800 mg.

II. Preparation of reducing terminal residue-limiting oxidized hyaluronic acid (O-HA)

1700 mg of the R-HA prepared in the above step A was dissolved in 250 ml of 40 mM imidazole hydrochloride (pH 6.5) and 139.96 mg of sodium periodate was added thereto at 0° C. followed by 1-hour of reaction. Ethanol was added to the reaction mixture and the precipitate thus formed was collected by filtration. The precipitate was dissolved in water and ethanol was added again to give a precipitate. Immediately thereafter, the precipitate (O-HA) was dissolved in a phosphate buffer solution or water and used in the reaction with a protein.

Lot No. 110-1.
Yield: 1600 mg.

III. Preparation of other reducing terminal residue-limiting oxidized glycosaminoglycans (O-GAG)

Hyaluronic acid [originating from comb: HA100 (MW 1,000,000)], chondroitin sulfate [originating from bovine tracheal cartilages: CS(T), shark cartilages: CS(S), whale cartilages: CS(W)], dermatan sulfate (originating from pig skin: DS), heparin (originating from pig intestinum tenue: Hep) and heparan sulfate (originating from pig kidney: HS) were treated in the same manner as in the above step A under the conditions as specified in Table 1. Thus reducing terminal residue-opened glycosaminoglycans (R-GAGs) were obtained. Subsequently, reducing terminal residue-limiting oxidized glycosaminoglycans (O-GAGs) were prepared in the same manner as in the above step B under the conditions as indicated in Table 2. Tables 1 and 2 also show the products thus-obtained and yield thereof.

TABLE 1

| Lot No. | Product | GAG/NaBH$_4$ (mg/mg) | Yield (mg) |
|---|---|---|---|
| 100-2 | R-HA | 5000/4.73 | 4720 |
| 101 | R-CS(T) | 1000/63.0 | 980 |
| 102 | R-CS(S) | 1000/31.5 | 897 |
| 103 | R-CS(W) | 1000/27.0 | 903 |
| 104 | R-Hep | 1000/63.1 | 888 |
| 105 | R-HS | 40/2.55 | 35.4 |
| 106 | R-DS | 150/9.46 | 130.4 |
| 107 | R-HA | 2000/1.82 | 1800 |

TABLE 2

| Lot No. | Product | R-GAG/NaIO$_4$ (mg/mg) | Yield (mg) |
|---|---|---|---|
| 110-2 | O-HA | 4500/3.852 | 4200 |
| 111 | O-CS(T) | 557.2/31.8 | 503.4 |
| 112 | O-CS(S) | 645.2/18.4 | 612.1 |
| 113 | O-CS(W) | 674.4/16.5 | 613.5 |
| 114 | O-Hep | 572.3/32.6 | 500.2 |
| 115 | O-HS | 26.6/1.52 | 25.0 |
| 116 | O-DS | 85.2/4.86 | 68.2 |
| 117 | O-HA | 1700/1.39956 | 1610 |

B Preparation of protein modified with reducing terminal residue-limiting oxidized glycosaminoglycan

I. Preparation of hyaluronic acid-modified catalase 100 mg of the product of lot No. 110-2 was dissolved in 10 ml of a 0.005M phosphate buffer solution (pH 8.0) and 2.3 mg of catalase originating from bovine liver (Seikagaku Corporation) was added thereto. The mixture was allowed to react at room temperature for 6 hours. Then, 0.4 mg of sodium cyanoborohydride was added thereto and the resulting mixture was allowed to react at room temperature for 20 hours. Then, the reaction mixture was filtered with an ultrafiltration device provided with a membrane of a fractionating molecular weight of 300,000 to remove low molecular weight substances. Then, the filtrate was purified with DEAE ion exchange resin chromatography and desalted with a dialysis membrane followed by lyophilization.

Figure 1A:
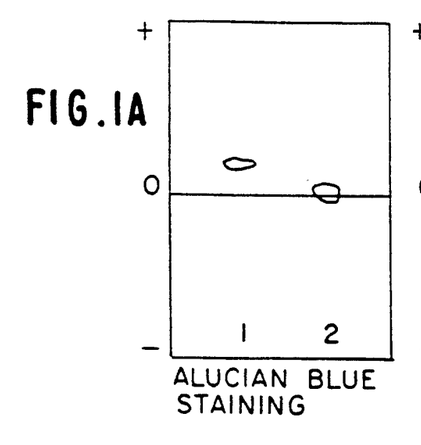
FIGS. 1A and B to 6A and B show each an electrophoretic pattern of the glycosaminoglycan-modified protein obtained in Examples and a mixture of a glycosaminoglycan and a protein.
Figure 1B:
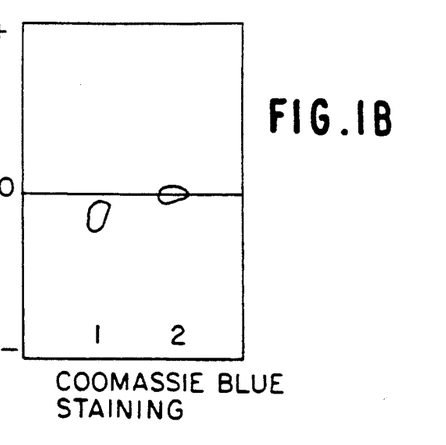

Lot No. 120-1.
Yield: 30.1 mg.
Catalase content: 2.1%.
Hyaluronic acid content: 97.9%.
Activity: 74.5% of that of unmodified catalase.
$[\alpha]_D$: $-78.0$ (C=1, $H_2O$).
Electrophoresis: cf. FIG. 1.
Acetylcellulose membrane (SEPARAX, JOOKOO Co., Ltd.)
0.1M formic acid/pyridine (pH 3.0)
0.5 mA/cm, 30 min.

and

In the above formulae, $P_1$ is a catalase residue exclusive of 11 amino acids, on an average, from catalase and X is a hydrogen atom of non-reducing terminal residue of hyaluronic acid.

II. Preparation of hyaluronic acid-modified catalase

Figure 2A:
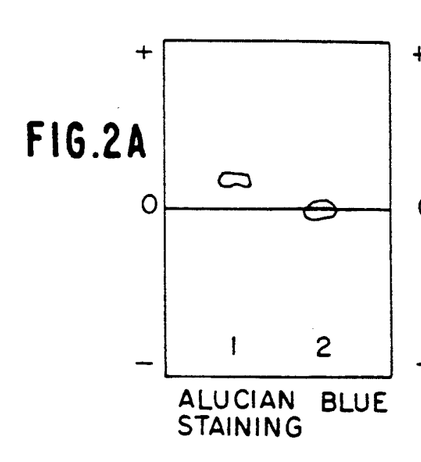
Figure 2B:
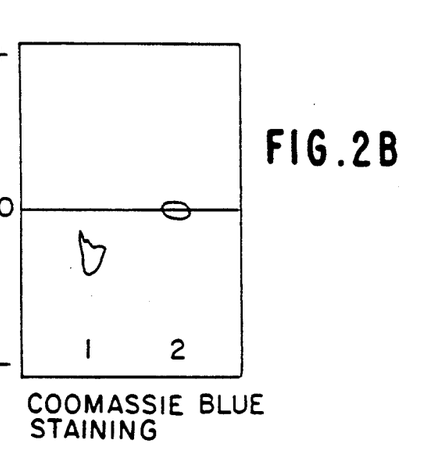

100 mg of the product of lot No. 110-2 and 1 mg of catalase derived from *Aspergillus niger* (Seikagaku Corporation) were prepared in the same manner as in the above I. The characteristics of the hyaluronic acid-modified catalase thus obtained were as follows:

Lot No. 120-2.
Yield: 29.0 mg.
Catalase content: 0.92%.
Hyaluronic acid content: 99.08%.
Activity: 85.1% of that of unmodified catalase.
$[\alpha]_D$: −78.8 (C=1, $H_2O$).
Electrophoresis: cf. FIG. 2.
Acetylcellulose membrane (SEPARAX, JOOKOO Co., Ltd.).
0.1M formic acid/pyridine (pH 3.0).

III. Preparation of hyaluronic acid-modified uricase 100 mg of the product of lot No. 110-2 was dissolved in 10 ml of a phosphate buffer solution (pH 8.0) and 2.5 mg of uricase originating from Candida (Seikagaku Corporation) was added thereto. The mixture was allowed to react at room temperature for 10 hours. Then, 0.4 mg of sodium cyanoborohydride was added thereto and the resulting mixture was allowed to react at room temperature for 20 hours. Ethanol was added to the reaction mixture and the precipitate thus formed was collected by filtration. Then, the precipitate was dissolved in water and purified with DEAE ion exchange resin chromatography. The characteristics of hyaluronic acid-modified uricase thus obtained were as follows:

Lot No. 120-3.
Yield: 23.5 mg.
Uricase content: 1.8%.
Hyaluronic acid content: 98.2%.
Activity: 73.4% of that of unmodified urikase.

and

In the above formulae, $P_2$ is a catalase residue exclusive of 26 amino groups, on an average, from catalase and X is as defined above.

Figure 3A:
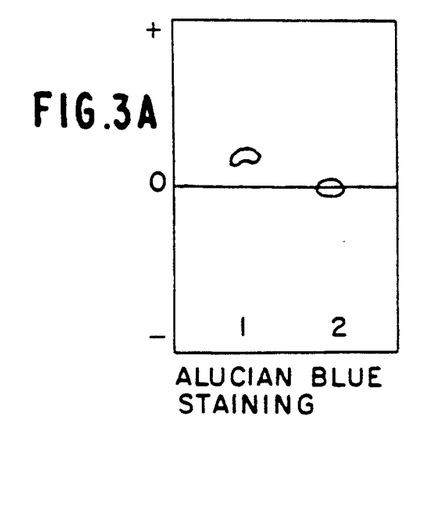
Figure 3B:
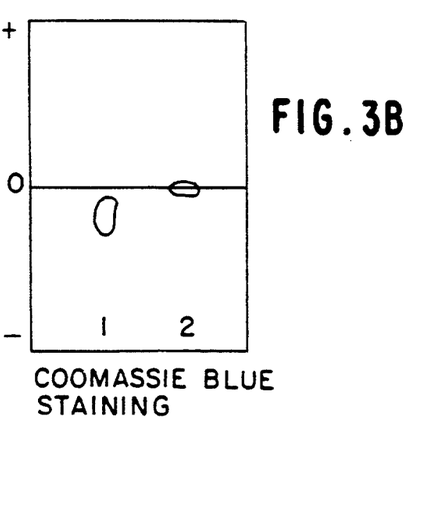

$[\alpha]_D$: −77.9 (C=1, $H_2O$).
Electrophoresis: cf. FIG. 3.
Acetylcellulose membrane (SEPARAX, JOOKOO Co., Ltd.)
0.1M formic acid/pyridine (pH 3.0)
0.5 mA/cm, 30 min.

and

In the above formulae, $P_3$ is a uricase residue exclusive of 5.5 amino groups, on an average, from uricase and X is as defined above.

Figure 4A:
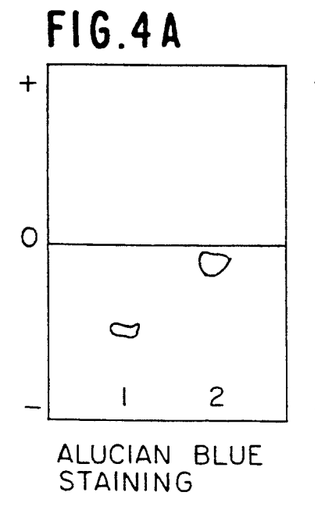
Figure 4B:
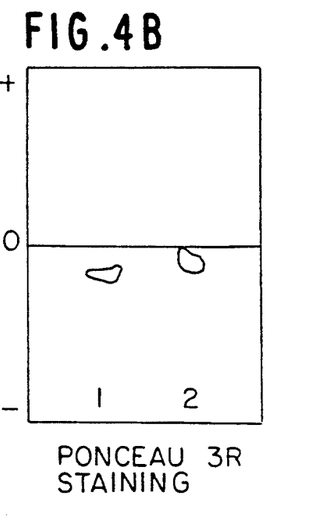

IV. Preparation of hyaluronic acid-modified asparaginase 100 mg of the product of lot No. 110-2 was dissolved in 10 ml of a 0.05M phosphate buffer solution (pH 8.0) and 5 mg of asparaginase originating from *Escherichia coli* (Kyowa Hakko Kogyo Co., Ltd.) was added thereto. The mixture was allowed to react at room temperature for 10 hours. Then, 1 mg of sodium cyanoborohydride was added thereto and the resulting mixture was allowed to react for 20 hours. Ethanol was added to the reaction mixture and the precipitate thus formed was collected by filtration. Then, the precipitate was dissolved in water and purified with DEAE ion exchange resin chromatography. The hyaluronic acid-modified asparaginase thus obtained was as follows:

Lot No. 120-4.
Asparaginase content: 4.8%.
Hyaluronic acid content: 95.2%.
Activity: 84.6% of that of unmodified asparaginase.
$[\alpha]_D$: $-76.9$ (C=1, $H_2O$).
Electrophoresis: cf. FIG. 4.
Acetylcellulose membrane (SEPARAX, JOOKOO Co., Ltd.)
0.069M veronal buffer solution (pH 8.6)
5 mA/cm, 40 min.

and

In the above formulae, $P_4$ is an asparaginase residue exclusive of 2.7 amino groups, on an average, from asparaginase and X is as defined above.

V. Preparation of hyaluronic acid-modified superoxide dismutase 100 mg of the product of lot No. 117 was dissolved in 10 ml of 0.05M phosphate buffer solution (pH 8.0) and 2.3 mg of superoxide dismutase (Sigma) originating from bovine red blood cell was added thereto. The mixture was allowed to react at room temperture for 20 hours. Then, 0.4 mg of sodium cyanoborohydride was added to the reaction mixture and the resulting mixture was allowed to react at room temperature for 2 hours. Ethanol was added to the reaction mixture to form a precipitate. The precipitate was washed well with ethanol and dried to obtain a hyaluronic acid-modified superoxide dismutase. The characteristics of this product are as follows.

Figure 6A:
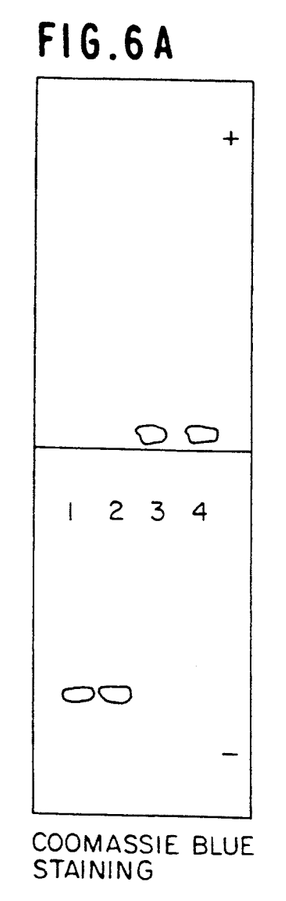
Figure 6B:
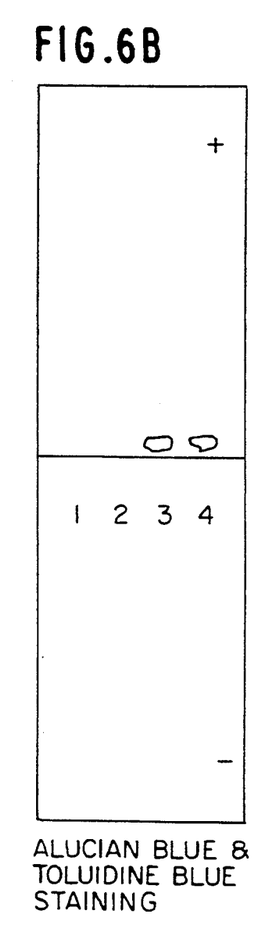
Figure 7:
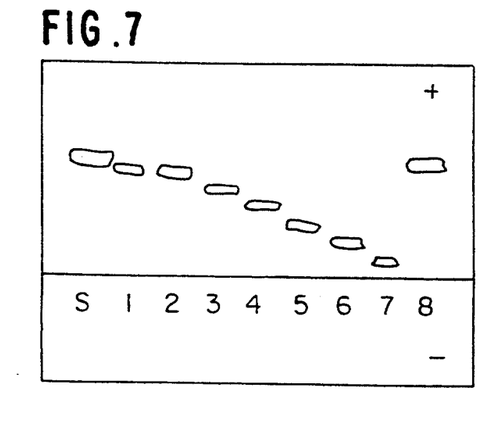
FIG. 7 shows an electrophoretic pattern of chondroitin sulfate described in Comparative Example.
Figure 8A:
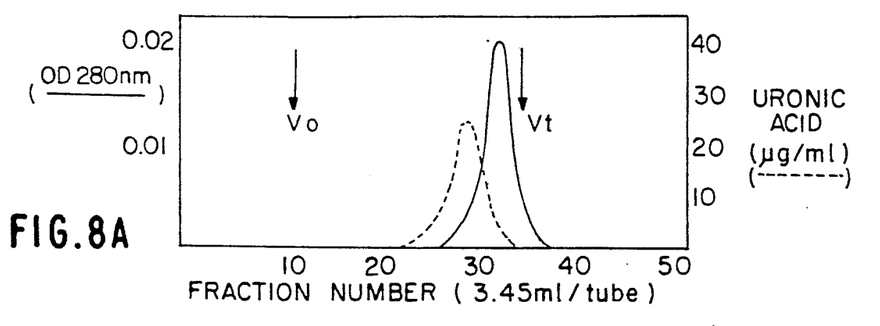
FIGS. 8A and B is chromatograms of gel filtration referred to in Comparative Example.
Figure 8B:
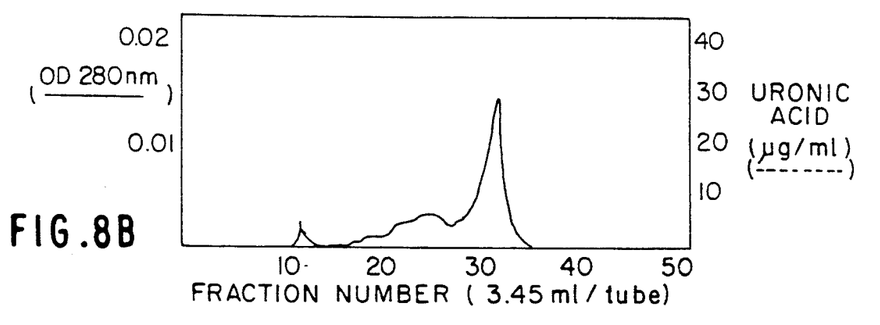
Figure 8C:
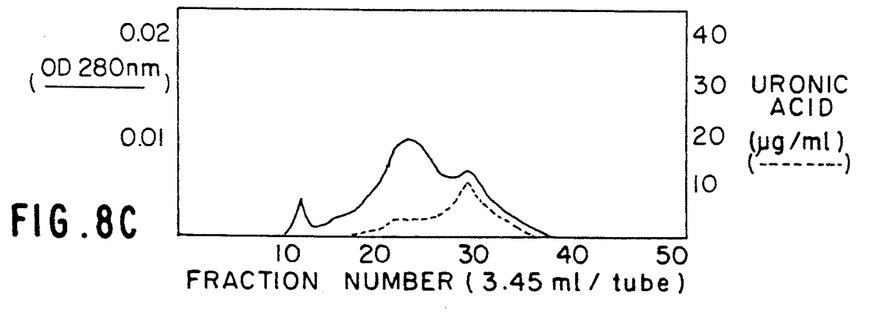
Figure 8D:
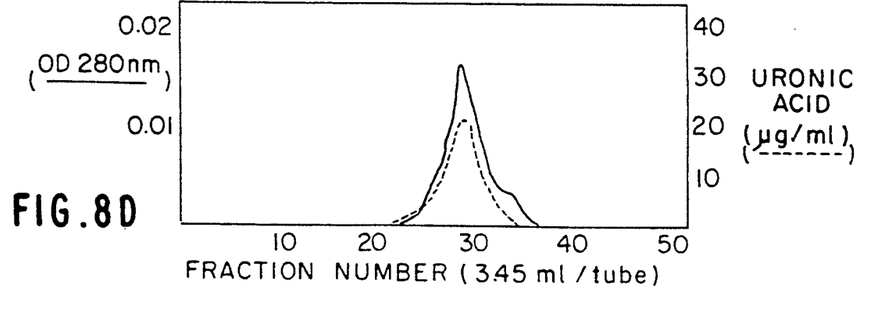

Yield: 89.7 mg
Superoxide dismutase content: 2.0%
Hyaluronic acid content: 98.0%
Molecular weight: 1,000,000
Activity: 89.8% of that of unmodified superoxide dismutase
$[\alpha]_D$: −78.0 (C=1, $H_2O$)
Electrophoresis: cf. FIG. 6

VI. Preparation of other glycosaminoglycan-modified proteins

Catalase originating from bovine liver, superoxide dismutase originating from bovine erythrocyte, hyaluronidase originating from bovine testis, lysozyme originating from albumen (the above enzymes are all manufactured by Seikagaku Corporation) and urokinase originating from human renal cell (Kyowa Hakko Kogyo Co., Ltd.) were modified with the products of lot Nos. 111 to 116 in the same manner as in the above step I under the conditions specified in Table 3. Table 4 shows the analytical data of the products thus obtained.

Figure 5A:
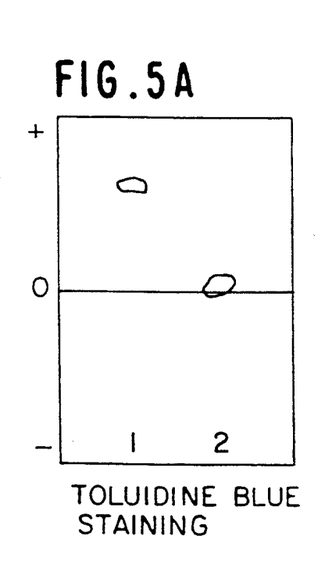
Figure 5B:
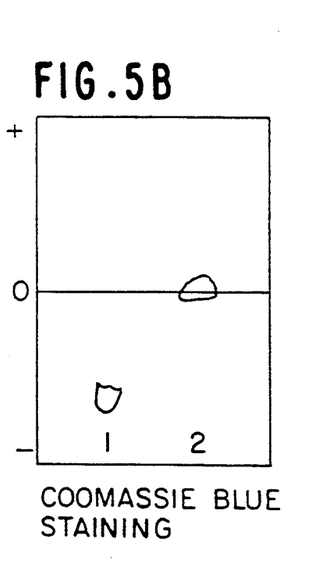

FIG. 5 shows the electrophoretic pattern of the product of lot No. 121-1 as a representative. The electrophoresis was conducted under the same conditions as those described in I.

TABLE 3

| Lot No. | Product | O-GAG/enzyme (mg/mg) |
| --- | --- | --- |
| 121-1 | CS(T)-catalase | 100/2 |
| 122 | CS(S)-catalase | 100/2 |
| 123 | CS(W)-catalase | 100/2 |
| 121-2 | CS(T)-superoxide dismutase | 25/2 |
| 124 | Hep-hyaluronidase | 100/5 |
| 125 | Hep-urokinase | 100/5 |
| 126 | DS-lysozyme | 10/0.5 |

TABLE 4

| Lot No. | Enzyme content (%) | Activity* | $[\alpha]_D$ |
| --- | --- | --- | --- |
| 121-1 | 1.98 | 82.4 | −22.4 |
| 122 | 1.88 | 80.9 | −18.4 |
| 123 | 1.92 | 80.7 | −28.7 |
| 121-2 | 11.67 | 69.9 | −19.0 |
| 124 | 4.77 | 78.6 | 56.3 |
| 125 | 4.29 | 77.3 | 57.2 |
| 126 | 4.90 | 78.9 | −54.7 |

Note:
*Expressed by referring the activity of unmodified enzyme as to 100.

VII. Immunological activity

Antigenecity of catalase originating from *Aspercillus niger* (Seikagaku Corporation) and the catalase modified with hyaluronic acid (lot No. 120-2) were examined in the following manner.

Catalase or HA-catalase dissolved in a 0.05M phosphate buffer solution of pH 7.0 (hereinafter abbreviated as PBS) was intraperitoneally (hereinafter abbreviated as i.p.) administered once a week for 12 weeks to female Swiss-Webster mice (each group has 4 animals) in a dose of 0.1 mg in terms of protein. On the 0, 3rd, 6th, 9th and 12th weeks, the blood of each animal was collected from the retoroorbital plexus and stored at −20° C. The titer of each serum was determined by HPO-ELISA (enzyme-linked immunosorbent assay with the use of horseradish peroxidase) in accordance with the method of Voller et al. 100 μl of an antigen solution diluted with a carbonate buffer solution (0.5 M, pH 9.5) to 10 μg/ml was used to inoculate wells of the Nunc Immuno II microtiter plates. The plate were incubated at 4° C. overnight and then washed with a physiological saline containing 0.05% of Tween 20 thrice. 100 μl of a test serum diluted with the Tween 20-containing PBS was added to each well. Three controls, i.e., an antigen control, an antiserum control and a normal mouse serum control were also prepared. After allowing to stand at room temperature for 1 hour, 100 μl portions of HPO-conjugated goat anti-mouse immunoglobulins (IgG+IgA+IgM) were added to each well and incubated at room temperature for 1 hour and 30 minutes. 100 μl of o-phenylenediamine substrate was added to each well and incubated for 10 minutes. Next, 0.01 ml of 4N sulfuric acid was added to cease the reaction. The titer is expressed in the antibody dilution ratio giving an optical density of 0.01 based on the control serum.

The results are shown in Table 5.

TABLE 5

| Sensitized antigen | Eliciting agent (1 μg protein) | Antigenicity (dilution ratio of antibody) |
| --- | --- | --- |
| Catalase | Catalase | 1:150000 |
| Catalase | HA-catalase | 1:4600 |
| HA-catalase | Catalase | 1:2500 |
| HA-catalase | HA-catalase | 1:1250 |

As shown in Table 5, the antigenicity or immunogenicity of HA-catalase is lower than that of unmodified catalase.

(VIII. Effect on mouse ischemic foot edema ($.O_2^-$ productivity by blood recirculation in hind leg ischemia)

A ddy male mouse aged 8 weeks is kept in a keeping device and the right hind leg is tied around with a suture (Brain No. 2). One end of the suture is fixed while a weight of 500 g is suspended from another end of the suture. Thus, ischemia is conducted for a definite period of time. Before the ischemia and 60 minutes thereafter, the thickness of the foot-pad of the animal was measured with slide calipers. Then, the foot-pad is cut and weighed. To a control group, a physiological saline is intravenously administered immediately before the initiation of the ischemia. To test groups, specimen shown in Table 6 was administered 30 minutes before the initiation of the ischemia and immediately before the same. Each group has 5 animals. The catarase used as a specimen was originated from bovine liver. The HA-catalase used was prepared as follows. 10 mg of the HA-catalase of lot No. 120-1 was dissolved in 5.2 ml of a physiological saline and filtered through a membrane of 0.22 μm (Milex GV; mfd. by Nippon Millipore Kogyo K.K.). 1 ml portions of the filtrate were distributed to ampuls to give a preparation for injection. The preparation contained 600 U of the enzyme per ampul.

The effects were calculated in accordance with the following equations.

Effect A:

-continued $$\text{Ischemic foot edema suppression ratio } (A) = \frac{\text{Sample [(ischemic foot-pad thickness)} - \text{(control foot-pad thickness)] (mm)}}{\text{Control [(ischemic foot-pad thickness)} - \text{(control foot-pad thickness)] (mm)}} \times 100$$

It is believed that a sample showing A of 40 or more is effective.

Effect B:

$$\text{Ischemic foot edema suppression ratio } (B) = \frac{\text{Sample [(ischemic foot-pad weight)} - \text{(control foot-pad weight)] (mg)}}{\text{Control [(ischemic foot-pad weight)} - \text{(control foot-pad weight)] (mg)}} \times 100$$

It is believed that a sample showing A of 60 or more is effective.

The results are shown in Table 6.

TABLE 6

| Test item | Effect A | Effect B |
|---|---|---|
| Control | 0 | 0 |
| Catalase (given 30 min. before ischemia) (10000 U/kg) | 18 | 38 |
| Catalase (given just before ischemia) (10000 U/kg) | 48 | 60 |
| HA-catalase (given 30 min. before ischemia) (2000 U/kg) | 47 | 55 |
| HA-catalase (given just before ischemia) (2000 U/kg) | 66 | 65 |
| (HA + catalase) given 30 min. before ischemia (HA 26.71 mg/kg + catalase 10000 U/kg) | 20 | 40 |
| (HA + catalase) given 30 min. before ischemia (HA 26.71 mg + catalase 10000 U/kg) | 30 | 41 |
| HA given just before ischemia (HA 26.71 mg) | 22 | 35 |

These results indicate that the unmodified catalase showed no effect while the HA-catalase was obviously effective when administered 30 minutes before the ischemia. From these results, it is presumed that the HA-catalase is stable in the blood and exerts a sustained activity.

IX. Preparation of chondroitin sulfate-modified ercatonin 100 mg of the product of the O-CS(T) of lot No. 111 was dissolved in 10 ml of a 0.05M phosphate buffer solution (pH 8.0) and 10 mg of ercatonin (Seikagaku Corporation) was added thereto. The mixture was allowed to react for 20 hours. Then the reaction mixture was filtered with an ultrafiltration device provided with a membrane of a fractionating molecular weight of 10,000 to remove the unreacted ercatonin followed by lyophilization. The characteristics of chondroitin sulfate-modified ercatonin thus obtained (lot No. 127) were as follows:

Yield: 98.2 mg
Ercatonin content: 5.50%.
Chondroitin sulfate content: 94.50%.
$[\alpha]_D$: −21.9 (C=1, $H_2O$).

and

In the above formulae, $P_5$ is an ercatonin residue exclusive of 2 amino groups, on an average, from ercatonin, X' is a hydrogen atom of the non-reducing terminal residue of chondroitin sulfate, $R_3$ and $R_4$ are not same and each represents —H or —$SO_2H$.

X. Activity and stability in blood of chondroitin sulfate-modified ercatonin (lot No. 127)

a) 5 μg/kg of ercatonin and 5 μg/kg, in terms of ercatonin, of chondroitin sulfate-modified ercatonin (lot No. 127) were administered to rats from the tail vein. The maximum decrease in the blood calcium level thus caused was referred to as 100. Then, the time required for achieving a decrease in the blood calcium level of 50 was measured. The results are as follows:

ercatonin: 48 hours; and
lot No. 127: 72 hours.

Thus, it was found out that the product of lot No. 127 would slowly exert its effect.

b) 5 μg/kg of ercatonin (27.6 μCi/mg) prepared from [1-$^{14}$C] alanine (50 mCi/mmol) and 5 μg/kg, in terms of ercatonin, of chondroitin sulfate-modified ercatonin (1.52 μCi/mg) prepared by modifying the ercatonin with the O-CS(T) of lot No. 111 were intravenously injected into rabbits. The concentration of each compound in the blood determined 2 minutes after the injection was referred to as 100 and the half-time was measured. The results are as follows:

| ercatonin: | 10 minutes; and |
| --- | --- |
| chondroitin sulfate-modified ercatonin: | 50 minutes. |

EXAMPLE 2

Preparation of GAG-modified protein by carboxyl group-activation method

A. Preparation of carboxyl group-activated glycosaminoglycan

I. Preparation of carboxyl group-activated hyaluronic acid a. 2800 mg of tri-n-butylamine salt of hyaluronic acid (MW 1,000,000) was dissolved in 280 ml of dimethylformamide. 0.17 ml of water-soluble carbodiimide [WSC 1-ethyl-3-(dimethylaminopropyl)-carbodiimide)] and 0.23 g of N-hydroxysuccinimide were added thereto and the mixture was allowed to react at room temperature for 20 hours. Ethanol saturated with sodium acetate was added to the reaction mixture and the precipitate thus formed was collected by filtration.
NS-HA lot No. 200.
Yield: 2500 mg.

b. 2800 mg of tri-n-butylamine salt of hyaluronic acid (MW 1,000,000) was dissolved in 280 ml of dimethylformamide. 0.17 ml of WSC and 0.27 g of N-hydroxybenzotriazole were added thereto and the resulting mixture was allowed to react at room temperature for 20 hours. The reaction mixture was treated in the same manner as described above.
NB-HA lot No. 200-1.
Yield: 2680 mg.

c. 2800 mg of tri-n-butylamine salt of hyaluronic acid was dissolved in 280 ml of dimethylformamide. 0.17 ml of WSC and 0 28 g of p-nitrophenol were added thereto and the obtained mixture was allowed to react at room temperature for 20 hours. The reaction mixture was treated in the same manner as in the above step a.
PN-HA lot No. 200-2.
Yield: 2775 mg.

from swine skin DS) were treated in the same manner as in the above step I under the conditions as specified in Table 7. The thus-obtained products are shown in Table 7.

TABLE 7

| Lot No. | Product | GAG (mg) | WSC (mg) | Activator | (mg) | Yield (mg) |
| --- | --- | --- | --- | --- | --- | --- |
| 200 | NS-HA | 2800 | 170 | N-hydroxysuccinimide | 230 | 2500 |
| 201 | NS-CS(T) | 1000 | 62.1 | N-hydroxysuccinimide | 44.4 | 975 |
| 202 | PN-CS(S) | 1000 | 62.1 | p-nitrophenol | 55.6 | 932 |
| 203 | NB-CS(W) | 1000 | 62.1 | N-hydrpoxybenzotriazole | 54.1 | 980 |
| 204 | NP-Hep | 1000 | 60.0 | N-hydroxypiperidine | 40.5 | 945 |
| 205 | NS-Hep | 1000 | 60.0 | N-hydroxysuccinimide | 44.4 | 900 |
| 206 | TP-DS | 1000 | 62.1 | 2,4,5-trichlorophenol | 79.0 | 965 |
| 207 | NS-HS | 100 | 6.0 | N-hydroxysuccinimide | 4.4 | 92 |

B. Preparation of protein modified with carboxy group-activated glycosaminoglycan I. Preparation of hyaluronic acid-modified catalase 100 mg of the product of lot No. 200 was dissolved in 20 ml of water and 2.5 mg of catalase originating from bovine liver (Seikagaku Corporation) was added thereto. The obtained mixture was allowed to react at room temperature at pH 7.0 for 20 hours. Then the reaction mixture was cooled to 0° C. and the pH value of the mixture was adjusted to 10.0 with 0.1N sodium hydroxide. Immediately thereafter, the mixture was neutralized with acetic acid and filtered with an ultrafiltration device provided with a membrane of a fractionating molecular weight of 300,000 to remove the unreacted catalase. The characterictics of the carboxyl group-activated hyaluronic acid-modified catalase thus obtained were as follows:
Lot No. 210.
Yield: 44 mg.
Catalase content: 2.3%.
Hyaluronic acid content: 97.7%.
Activity: 84.3% of that of unmodified catalase.
$[\alpha]_D$: −77.9 (C=1, H$_2$O).

II. Preparation of carboxyl group-activated glycosaminoglycan

Chondroitin sulfate [originating from bovine tracheal cartilages: CS(T), shark cartilages: CS(S), whale cartilages: CS(W)], heparin (originating from swine intestinum tenue: Hep), heparan sulfate (originating from swine kidney: HS) and dermatan sulfate (originating wherein P$_6$ is a catalase residue exclusive of 10 amino groups, on an average, from catalase, Y is a hydrogen atom of the reducing terminal residue of hyaluronic acid, X is as defied above and the sum of n, m and l is 2,500.

II. Preparation of chondroitin sulfate-modified superoxide dismutase 100 mg of the product of lot No. 201 and 2.5 mg of superoxide dismutase originating from bovine erythrocyte (Seikagaku Corporation) were reacted in the same manner as in the above I. The characteristics of the carboxyl group activated chondroitin sulfate-modified superoxide dismutase thus obtained were as follows:

Lot No. 211.
Yield: 41.2 mg.
Superoxide dismutase content: 2.0%.
Chondroitin sulfate content: 98.0%.
Activity: 81.4% of that of unmodified superoxide dismutase.
$[\alpha]_D$: −78.0 (C=1, $H_2O$).

wherein $P_7$ is a superoxide dismutase residue exclusive of 80 amino groups, on an average, from superoxide dismutase, Y' is a hydrogen atom of the reducing terminal residue of chondroitin sulfate, the sum of n, m and l is 40 and X' $R_3$ and $R_4$ are as defined above.

EXAMPLE 3

Preparation of GAG-modified protein by reducing terminal residue-lactonization method A. Preparation of reducing terminal residue-lactonized hyaluronic acid 500 mg of hyaluronic acid (MW 10,000) was dissolved in 50 ml of water. 5 ml of a 0.1M iodine solution in methanol was added thereto and the resulting mixture was allowed to react at room temperature for 6 hours. Then, approximately 5 ml of 0.1N potassium hydroxide was added to the reaction mixture so as to cause the discoloration of the liberated iodine. Ethanol saturated with potassium acetate was added to the solution. The precipitate thus formed was collected by filtration and dissolved in 50 ml of water. The resulting solution was contacted with 50 ml of a strongly acidic ion exchange resin [Dowex 50(H+)] at 5° C. for 20 hours. The filtrate thus obtained was neutralized with tri-n-butylamine. The excessive amine was removed with ether and the residue was lyophilized. Thus, tri-n-butylamine of reducing terminal residue-lactonized hyaluronic acid was obtained as white powder.

Lot No. 310.
Yield: 410 mg.
Reducing sugar determined by Somogyi-Nelson's method: none.

B. Preparation of protein modified with reducing terminal residue-lactonized glycosaminoglycan I. Preparation of hyaluronic acid-modified peptide (H-Arg-Gly-Asp-Val-$NH_2$; RGDV):

60 mg of the product of lot NO. 310 was dissolved in 20 ml of dimethylformamide and 2.5 mg of a dimethylformamide solution of RGDV was added thereto. The resulting mixture was allowed to react at 60° C. for 2 hours. 10 ml of a 25% aqueous solution of sodium acetate was added to the reaction mixture and the resulting mixture was allowed to stand at room temperature for 30 minutes. Then, ethanol was added thereto and the precipitate thus formed was collected by filtration. The filtrate was treated with an ultrafiltration device provided with a membrane of a fractionating molecular weight of 5000 to remove the unreacted RGDV. Then, the filtrate was lyophilized. The characteristics of hyaluronic acid-modified RGDV were as follows:

Lot No. 320.
Yield: 40.2 mg.
RGDV content: 3.3%.
Hyaluronic acid content: 96.7%.

and

-continued

In the above formulae, X is as defined above.

EXAMPLE 4
Preparation of hyaluronic acid-modified superoxide dismutase 400 mg of comb-derived hyaluronic acid (MW 150,000) was dissolved in 2M phosphate buffer (pH 11.5) and 1 ml of an acetonitrile solution of cyanogen bromide (100 mg/ml) was added thereto to allow the resulting mixture to react at 4° C. for 5 minutes. Immediately after the termination of the reaction, 150 ml of acetonitrile was added to the reaction mixture to form precipitate. The thus-obtained precipitate was washed quickly with acetonitrile and was dissolved in 0.1M sodium hydrogencarbonate solution. 10 ml of a 1% solution of superoxide dismutase (SOD) derived from dog red blood cell was added to the reation mixture and the reaction was carried out at 4° C. for 20 hours. Ethanol was added to the reaction mixture to form precipitate and the resulting precipitate was dissolved in water. After adding 0.1 ml of ethanol amine to the mixture, the reaction was carried out at room temperature for one hour. Ethanol was added to the reaction mixutre to obtain precipitate and the thus-obtained precipitate was washed with ethanol well and dried to obtain hyaluronic acid-modified SOD.

The characteristics of the hyaluronic acid-modified SOD thus obtained were as follows.
Yield: 350 mg
SOD content: 21.2%.
Hyaluronic acid content: 78.8%
Molecular weight: 172,000
Activity: 82.1% of that of unmodified SOD
Electrophoresis: cf. FIG. 6.

COMPARATIVE EXAMPLE

Comparison of chondroitin sulfate-modified superoxide dismutase of U.S. Pat. No. 4,585,754 with the present invention A) Formation of chondroitin sulfate with the use of water-soluble carbodiimide 25 mg of chondroitin sulfate originating from bovine tracheal cartilages [CS(T)] was dissolved in 10 ml of water and the pH value of the resulting solution was adjusted to 5.0 with 0.1N hydrochloric acid. Then, 0.0436, 0.145, 0.436, 1.45, 4.36, 14.5 and 43.6 mg of water-soluble carbodiimide [WSC; 1-ethyl-3-(dimethylaminopropyl)carbodiimide hydrochloride] was added thereto. Each mixture thus obtained was allowed to react at room temperature for 6 hours. Then, the reaction mixture was dialyzed against a 0.015M phosphate buffer solution (pH 7.0) and subjected to electrophoresis with the use of a cellulose acetate membrane [0.1M pyridine/formic acid buffer solution (pH 3.0), 30 minutes, 0.5 mA/cm. Further, the reaction product, to which 43.6 mg of WSC had been added, was mixed with 0.1N aqueous solution of sodium hydroxide, treated for 1 hour and then subjected to electrophoresis. As a result, it was found out that the CS(T) per se was obviously esterified (cf. FIG. 6).

B) Identification of the polymerization of SOD per se with water-soluble carbodiimide and chondroitin sulfate-modified SOD polymer 5 mg of SOD was dissolved in 10 ml of water and the pH value of the resulting solution was adjusted to 5.0 with 0.1N hydrochloric acid. Then, 2.5 mg of WSC was added thereto and the resulting mixture was allowed to react at room temperature for 6 hours. Then, it was dialyzed against a 0.015M phosphate buffer solution (pH 7.0). The aqueous solution thus obtained was referred to as lot No. B.

In accordance with U.S. Pat. No. 4,585,754, separately, 25 mg of CS(T) was dissolved in 10 ml of water and the pH value of the resulting solution was adjusted to 5.0. Then, 5 mg of SOD and 12.5 mg of WSC were added thereto and the mixture was allowed to react at room temperature for 6 hours. This reaction mixture was treated in the same manner as in the above step A). The aqueous solution thus obtained was referred to as lot No. C.

C) Difference in gel chromatographic elution pattern

Each product obtained above was subjected to gel filtration using a Sepharose CL4B (Pharmacia, Sweden; 1.2×100 cm) column with the use of a 0.05M phosphate buffer solution (pH 7.0) containing 0.3M sodium chloride as a developing solvent. The eluate was collected in 3.45 ml portions in tubes. FIG. 8 shows the results of the gel filtration.

As shown in FIG. 8, it was found that a reaction between a protein carrying both of a carboxyl group and an amino group (SOD in this case) with chondroitin sulfate in the presence of WSC would give a polymer of a complicated structure as a reaction product.

Further, the activity of the WSC-modified SOD is lower than the glycosaminoglycan-modified SOD of the present invention, though the contents of SOD are the same as each other.

| | |
|---|---|
| WSC method (lot No. B): | 44.4% of the activity of unmodified SOD. |
| Invention method (lot No. 121-2:D): | 69.9% of the activity of unmodified SOD. |

While the invention has been described in detail and with reference to specific embodiments thereof, it will be apparent to one skilled in the art that various changes and modification can be made therein without departing from the spirit and scope thereof.

What is claimed is:

1. A glycosaminoglycan-modified protein represented by the formula:

wherein P represents a protein residue exclusive of n amino groups from the protein; n is an integer of from 1 to 100; and GAG represents a glycosaminoglycan residue exclusive of a reducing terminal sugar moiety from the glycosaminoglycan.

2. The glycosaminoglycan-modified protein according to claim 1, wherein the glycosaminoglycan content ranges from 1 to 99.9% by weight based on the weight of the protein.

3. The glycosaminoglycan-modified protein according to claim 1, wherein the glycosaminoglycan is selected from the group consisting of colominic acid, hyaluronic acid, chondroitin, chondroitin sulfate, teichuronic acid, dermatan sulfate, heparin, heparan sulfate, keratosulfate and keratopolysulfate.

4. A process for the production of a glycosaminoglycan-modified protein of claim 1, which comprises activating a glycosaminoglycan by partially oxidizing the reducing terminal sugar moiety of said glycosaminoglycan to thereby cleave the terminal sugar moiety followed by forming a lactone therefrom and reacting the activated glycosaminoglycan with a protein.

5. A pharmaceutical composition containing a glycosaminoglycan-modified protein of claim 1, and a pharmaceutically acceptable carrier or diluent.

6. A glycosaminoglycan-modified protein wherein a reducing terminal sugar moiety of the glycosaminoglycan is cleaved and a functional group of the reducing terminal sugar moiety-cleaved glycosaminoglycan is bound to an amino group of a protein via a covalent bond.

7. A glycosaminoglycan-modified protein wherein an amino group of a protein is bound to a carbonyl group of the glycosaminoglycan, which has been formed by oxidizing a reducing terminal sugar moiety of a glycosaminoglycan and treating the reducing terminal sugar moiety-oxidized glycosaminoglycan with an acid.

* * * * *